United States Patent [19]

Kaufhold et al.

[11] 3,968,177

[45] July 6, 1976

[54] METHOD FOR PREPARING STRAIGHT-CHAIN PRIMARY ALCOHOLS

[75] Inventors: Manfred Kaufhold; Harald Kett, both of Marl, Germany

[73] Assignee: Chemische Werke Huls Aktiengesellschaft, Marl, Germany

[22] Filed: Sept. 11, 1974

[21] Appl. No.: 505,044

[30] Foreign Application Priority Data

Sept. 19, 1973   Germany............................ 2347095

[52] U.S. Cl...................... 260/638 R; 260/410.9 N; 260/493; 260/652 P; 260/660
[51] Int. Cl.²......................................... C07C 29/00
[58] Field of Search................ 260/493, 660, 652 P, 260/638 R

[56] References Cited
UNITED STATES PATENTS

| | | | |
|---|---|---|---|
| 1,430,324 | 9/1922 | Rodebush............................ | 260/493 |
| 1,962,941 | 6/1934 | Schrauth.......................... | 260/638 R |
| 2,049,207 | 7/1936 | Lawson................................ | 260/493 |
| 2,245,538 | 6/1941 | Thurman.......................... | 260/638 R |
| 2,444,129 | 6/1948 | Bearse et al. ....................... | 260/493 |
| 3,240,834 | 3/1966 | Kruse et al. ...................... | 260/652 P |
| 3,277,204 | 10/1966 | Ferstandig et al. ................. | 260/660 |
| 3,294,851 | 12/1966 | Roobol et al..................... | 260/652 P |
| 3,510,500 | 5/1970 | Walsh ................................ | 260/493 |
| 3,655,701 | 4/1972 | Darre................................. | 260/493 |

Primary Examiner—Joseph E. Evans
Attorney, Agent, or Firm—Gilbert L. Wells

[57] ABSTRACT

Straight-chain, primary alcohols are prepared by reacting straight-chain 1-chloroalkanes having 6 to 20 carbon atoms with alkali salts of monocarboxylic acids having 4 to 22 carbon atoms in the presence of 1 to 10 mole percent of monocarboxylic acids or alcohols based upon the alkali salt of the carboxylic acid and at temperatures ranging from 150° to 300°C. The esters formed are saponified in alkaline medium to the straight-chain, primary alcohols and separated.

8 Claims, No Drawings

METHOD FOR PREPARING STRAIGHT-CHAIN PRIMARY ALCOHOLS

BACKGROUND OF THE INVENTION

The field of the invention is straight-chain, primary alcohols.

Alcohols, especially straight-chain, primary alcohols, are suitable basic materials for detergents, emulsifiers, lubricating oils, etc. Further, straight-chain, primary alcohols are converted for instance by means of ethylene oxide to easily biologically degradable ethoxylates. Also, esterifications for instance by means of sulfur trioxide provide better yields than in branched alcohols.

The state of the art of preparing straight-chain, primary alcohols may be ascertained by reference to U.S. Pat. No. 3,401,206 of Horst-Dieter Wulf and Karl Geifert, which issued Sept. 10, 1968, and the Kirk-Othmer "Encyclopedia of Chemical Technology," 2nd Ed., Vol. 1 (1963), pp. 560–569, under the section Alcohols, Higher, Synthetic; Vol. 5 (1964), pp. 231–240, under the section Chlorinated Paraffins; and Vol. 8 (1966), pp. 356–361, under the section Ester Interchange, wherein alcoholysis in the presence of an alkaline catalyst is disclosed; the disclosures of which are incorporated herein.

Oxosynthesis is a process for preparing straight-chain, primary alcohols (see Ullmann's Enzyklopaedie der technischen Chemie, 3rd Ed., complementary volume, pp 87–92). Oxosynthesis is always accompanied by an undesirable by-product in the form of the branched aldehyde, possibly following hydrogenation of the alcohol. The proportion of straight-chain compounds in the reaction mixture in all prior art processes employed so far has been less than 90 percent. Straight-chain, primary alcohols also are prepared by the so-called aluminum foil or Alfol process of K. Ziegler (see Ullmann's Enzyklopaedie der technischen Chemie, 3rd Ed., complementary volume, pp. 92-4, and Kirk-Othmer, ibid, Vol. 1, p. 560). Aluminum alkyls with higher, unbranched alkyl groups are obtained, which may be transformed by air oxidation and subsequent hydrolysis of the aluminum alkoxides into a mixture of unbranched and straight-chain alcohols of various chain lengths. The drawback of this latter process is the great variation in length of the chains of the generated alcohols.

SUMMARY OF THE INVENTION

It is an object of the present invention to find a process for preparing primary, straight-chain alcohols with 6 to 20 carbon atoms, wherein the occurrence of isomeric by-products and of products of different chain lengths is avoided. The present invention achieves this objective by reacting primary, straight-chain 1-chloroalkanes having 6–20 carbon atoms with the alkali salts of monocarboxylic acids having 4 to 22 carbon atoms in the presence of 1–10 mole percent of monocarboxylic acids or alcohols, based on the alkali salt of the monocarboxylic acid and at temperatures of 150°–300°C, and by saponifying in alkaline medium according to the prior art, the esters so formed and separating the alcohols so occurring.

Ester preparation takes place according to the prior art by reacting an alkali salt of a carboxylic acid with 1-chloroalkanes. It is surprisingly found that the rate of ester formation is very favorably affected by minor additions of carboxylic acids or alcohols. Addition of about 1–10 mole percent of carboxylic acid or alcohol with respect to the alkali salt of the monocarboxylic acid suffices. Preferably from about 2 to 10 mole percent is added. For less than 1 mole percent, the reaction rate drops excessively, while above 10 mole percent, it can hardly be affected. Appropriately, only such alcohols are added which are to be prepared or which will remain as residues in recovery. Correspondingly, those acids are most suitable of which the alkali salts are used as the ester components.

In order to achieve sufficiently high reaction rates in ester formation, one operates above temperatures of 150°C, preferably at 200°–250°C. Above 300°C, ester pyrolysis generating olefins and acids decreases ester yields as temperature increases. Depending on the temperature range, the reaction is terminated in about 2–4 hours.

DESCRIPTION OF THE PREFERRED EMBODIMENTS

In conformity with the present invention, use is made of straight-chain 1-chloroalkanes with 6 to 20 carbon atoms. The temperatures required for ordinary reaction times (2–4 hours) cannot be achieved at standard pressure for straight-chain 1-chloroalkanes with fewer than 6 carbon atoms. Furthermore, the preparation of 100 percent straight-chain alcohols is easily feasible in this range of carbon atoms by means of oxosynethesis. Rectilinear chain 1-chloroalkanes with more than 20 carbon atoms are difficult to handle because of their high boiling points and the related easy decomposition in the boiling point range. The carboxylic acids or their alkali salts used, preferably their sodium salts, are carboxylic acids with 4 to 22 carbon atoms. Preferably use is made of sodium salts with 4 to 10 carbon atoms. If sodium acetate or sodium propionate with addition of acetic acid or of propionic acid respectively are used as ester components, conversion is only minor. When carboxylic acids with more than 10 carbon atoms are used as ester components, then bothersome foaming, due to the alkali salts of higher fatty acids formed, accompanies the alkaline saponification of the ester. Particularly advantageous is the use of those carboxylic acids of which the sodium salts are very easily soluble in the chlorine compounds to be reacted and this consideration applies for instance to 2-ethylhexanoic acid. The salts of these acids may be used as non-aqueous solutions in organic solvents or reaction products for ester formation, and are obtained again as such following the alkaline saponification, and are especially easy to handle as pumped solutions. Saponification of the esters prepared in conformity with the invention takes place in conventional manner, generally by adding aqueous solutions of an alkaline or earth alkaline hydroxide, preferably sodium hydroxide. A substance of higher boiling point than the alcohol obtained and easily separated from it by distillation is added to the mixture following saponification. Examples of this are a residue of an oxo-alcohol or one occurring in the aluminum foil process. Thereupon there is direct distillation, the water being transmitted being separated as a first run. Following distillation of the alcohol, the solution of the alkali salt from the carboxylic acid being used is obtained in the sump as the high boiling point oxo-alcohol or aluminum foil residue. This salt solution may be used again for ester formation. One may also dilute for instance the reaction mixture with an organic solvent such as cyclohexane, or wash it with water, and subsequently one may recover the organic phase by distillation. The desired alcohols are obtained by distillation. When using this procedure, the alkali salts of the carboxylic acid again are obtained as an aqueous solution and may be used again for ester formation.

The process of the invention further allows preparing predominantly primary, straight-chain alcohols with good yields from mixtures containing predominantly straight-chain 1-chloroalkanes. It was found that there are predominantly straight-chain 1-chloroalkanes besides other products in the sumps of dissociation reactors wherein chloroalkanes are decomposed into olefins and hydrochloric acid, as disclosed in U.S. Pat. No. 3,401,206.

As regards this process, n-paraffins are chlorinated to a chlorine content of about 30 mole percent. Then the chlorinated paraffins so obtained are dehydrochlorinated in a reactor filled with iron bodies at a temperature of 200°–400°C. When the olefins generated in this process and the non-converted paraffins, further the non-identified impurities, are removed and eliminated from the reactor, then the straight-chain 1-chloroalkanes increase in the reactor sump because of their higher boiling points and their lesser reactivity.

There is constant product removal from the sump of the dissociation reactor and distillation, in continuous operation, in order to separate the 1-chloroalkanes from the tar-like products. If the entire chlorination product is used for the preparation of olefins, then the entire distillate is fed back into the reactor. If, however, only part is used for alcohol preparation, then the distillate is only partly tapped.

The composition of the distillate is complex and part of the components could not be identified. Example 6 of the present invention describes enrichment in straight-chain 1-chloroalkanes in the distillation of a chloroalkane isomer mixture, wherein part of the chlorine compounds are dehydrochlorinated. When this operation is repeated several times, the effect is enhanced so much that a base-product suitable for preparing straight-chain alcohols is obtained.

The process of the present invention allows preparing in surprisingly simple manner primary, straight-chain alcohols by esterification of straight-chain 1-choroalkanes and alkali salts of monocarboxylic acids with addition of alcohols or carboxylic acids, without there occurring any isomerization. Further, the process of the present invention allows surprisingly smooth reactive preparation of straight-chain, primary alcohols from intermediate products obtained from the preparation of dehydrochlorination olefins.

Specific examples of the 1-chloroalkanes having 6–20 carbon atoms and useful in the present invention have a chlorine content of about 11 to 29 percent and include, but are not limited to:

lauryl chloride, 1-chloro-undecane, n-hexyl-chloride, 1-chloro-C20 alkane, 1-chloro-C22 alkane, mixtures of C-11 to C-14 1-chloroalkanes, 1-chloro-octane, 1-chloro-nonane, 1-chloro-decane, 1-chloro-tridecane, 1-chloropentedecane, 1-chloro-hexadecane, 1-chloro-heptadecane, 1-chloro-nonadecane and mixtures thereof, mixtures of 1-chloro-alkanes, which are commercially obtainable, e.g. 1-chloro-C11 alkane mixture, 1-chloro-C12 alkane mixture, 1-chloro-C13 alkane mixture, 1-chloro-C14 alkane mixture and the like.

Specific examples of the alkali salts of monocarboxylic acids having 4–22 carbon atoms and useful in the present invention include, but are not limited to: sodium salt of 2-ethylhexanoic acid, sodium salt of caprylic acid, sodium salt of behenic acid, sodium salt of isobutyric acid, sodium salt of n-butyric acid, sodium salt of i-valeric acid, sodium salt of n-valeric acid, sodium salt of i-capronic acid, sodium salt of n-capronic acid, sodium salt of i-oenanthic acid, sodium salt of n-oenanthic acid, sodium salt of i-caprylic acid, sodium salt of i-pelargonic acid, sodium salt of n-pelargonic acid, sodium salt of i-capric acid, sodium salt of n-capric acid, sodium salt of i-undecanoic acid, sodium salt of n-decanoic acid, sodium salt of lauric acid, sodium salt of a branched chain C12 acid, sodium salt of n-tridecanoic acid, sodium salt of a branched chain C13 acid, sodium salt of myristic acid, sodium salt of a branched chain C14 acid, sodium salt of daturic acid, sodium salt of a branched chain C15 acid, sodium salt of palmitic acid, sodium salt of a branched chain C16 acid, sodium salts of straight or branched chain heptadecanoic acids, sodium salt of stearic acid, sodium salt of a branched chain C18 acid, sodium salt of straight or branched chain nonedecanoic acid, sodium salt of arachic acid, sodium salt of branched chain C20 acid, sodium salt of behenic acid, sodium salt of branched chain C22 acid. Instead of these sodium salts the potassium, magnesium, calcium or barium salts may also be used.

Specific examples of the monocarboxylic acids useful in the present invention and having 4 to 22 carbon atoms include, but are not limited to: 2-ethylhexanoic acid, caprylic acid, n- and i-butyric acid, n-and i-valeric acid, n- and i-capronic acid, n- and i-oenanthic acid, i-caprylic acid, n-caprylic acid, n- and i-pelargonic acid, n- and i-capric acid, n- and i-undecanoic acid, n- and i-dodecanoic acid, n- and i-tridecanoic acid, myristic acid, branched chain C14 acid, daturic acid, branched chain C15 acid, palmitic acid, branched chain C16 acid, straight chain and branched chain C17 acid, stearic acid, branched chain C18 acid, straight chain and branched chain C19 acid, arachic acid, branched chain C20 acid, straight and branched chain C21 acid, behenic acid and branched chain C22 acid. If the free acid is not identical with the acid of the sodium salt, a mixture of esters of the different acids is formed. If the boiling points of the formed esters are too different this may cause difficulties in the distillation step.

Specific examples of the alcohols useful in the present invention and having 6 to 20 carbon atoms include, but are not limited to: tallow fat alcohol, straight and branched chain C6 alcohols, straight and branched chain C7 alcohols, straight and branched chain octanols, straight and branched chain nonanols, straight and branched chain decanols, straight and branched chain undecanols, straight and branched chain dodecanols, straight and branched chain C13 alcohols, straight and branched chain C14 alcohols, straight and branched chain C15 alcohols, straight and branched chain C16 alcohols, straight and branched chain C17 alcohols, straight and branched chain C18 alcohols, straight and branched chain C19 alcohols, straight and branched chain C20 alcohols. Preferably those alcohols are used, which by their high boiling point allow the use of high temperatures without pressure during the esterification reaction and which can be separated by distillation from the formed mean- and by-product.

The esterification reaction of the present invention is carried out at a temperature of about 150°–300°C, preferably 200°–250°C, for a period of about 10 minutes to 5 hours, preferably 1 to 2 hours.

The examples below further illustrate and explain the present invention.

EXAMPLE 1.

245 gm (1.2 mole) of pure lauryl chloride were stirred with 166 gm (1.0 mole) of neutral sodium salt of the 2-ethylhexanoic acid and heated. The salt was dissolved starting at about 100°C and the solution clouded when further heated to 220°C. After stirring the mixture for 2 hours at 220°C, a sample was removed in the oil phase, this sample then being washed with water and the chlorine value was determined. It was found to be 13.3 percent, that is, a little below that of the base material; conversion amounted to only 23.5 percent (the base material's chlorine content was 17.4 percent).

Thereupon 1 mole percent of 2-ethylhexanoic acid referred to the sodium salt of the 2-ethylhexanoic acid is added and the mixture is stirred again at 220°C for 2 hours. Following cooling, the precipitated sodium chloride is removed from the oil phase by washing with water and the dried phase is distilled. After removing the first run, pure ester is obtained with a yield of 93 percent of theoretical.

EXAMPLE 2

(Reacting lauryl chloride with the sodium salt of caprylic acid)

332 gm (2 moles) of the sodium salt of caprylic acid with an acid number of 4.0, together with 502 gm (2.5 moles) of lauryl chloride and 15 gm of caprylic acid were heated for 2.5 hours to 230°C while stirring. The mixture increasing in viscosity and, causing difficulties in stirring, the temperature was further raised for 3 hours to 250°C. Following cooling, washing is undertaken by means of water and sodium hydroxide (25 percent), (and then) distillation. 570 gm of ester are obtained, representing a yield of 91.7 percent of theoretical.

EXAMPLE 3

282 gm of n-hexylchloride (2.35 moles) are used and added dropwise at 120°–140°C to 507 gm of a 73.9 percent aqueous solution of the sodium salt of the 2-ethylhexanoic acid (2.25 moles) and 10 gm of 2-ethylhexanoic acid while stirring, i.e., water is taken out of circulation. The temperature is raised as follows: from 140° to 155°C in the first five hours, then from 155° to 180°C in the next five hours and from 180° to 220°C in the five hours thereafter. Following cooling, the sodium chloride generated is washed off with 700 ml of water and the excess acid with 32 gm of 25 percent sodium hydroxide. Distillation at 25 torr (mm Hg) and 144°C yields 493 gm of ester of 96 percent of theoretical. Saponification is undertaken in conventional manner by dropwise addition of 50 percent sodium hydroxide at 130° C and subsequent two hour boiling at reflux; n-hexanol is obtained in a yield of 97 percent of theoretical.

EXAMPLE 4

A mixture consisting of 52 percent of 1-chloro-C 20 alkane and 48 percent of 1-chloro C 22 alkane and of a chlorine content of 9.88 percent is used.

300 gm (1.24 mole) of 73.9 percent aqueous solution of the sodium salt of the 2-ethylhexanoic acid and 5 gm of 2-ethylhexanoic acid are added to 447 gm (1.24 moles, computed from the chlorine content) of said mixture while stirring at 200°C, so that water is taken out of circulation. This is followed by four hours of stirring at 220°C.

Following cooling, the generated sodium chloride is washed off with one liter of water and the excess acid with 30 gm of 25 percent sodium hydroxide. The chlorine content of the reaction product is 1.02 percent and indicated a conversion of 89.7 percent. Slight decomposition occurs during ester distillation because of the high boiling point.

EXAMPLE 5

The poor solubility of the sodium salt of behenic acid $[CH_3(CH_2)_{20}COOH]$ in water and in chloroalkanes requires some modification in procedure:

415 gm (1.1 mole) of behenic acid (90 percent) are mixed with 80 gm (1.0 mole) of 50 percent sodium hydroxide, with 2 liters of water and 2 liters of ethanol and boiled at reflux until a clear solution is obtained. The solution is evaporated to dryness, 1,133 gm of a solid salt with an acid number of 7.15 still containing water but amenable to further processing in this form is obtained.

1,128 gm of the solid are mixed with 523 gm (3.52 moles) of octylchloride; 700 ml of water are taken out of circulation while stirring at 140°–190°C and by means of the octylchloride. Thereupon stirring is carried out for five hours at 190°C.

Following cooling, the sodium chloride so generated is washed off with 300 gm of water at 40°C. The excess behenic acid could not be washed out with sodium hydroxide. For that reason, the reaction product was absorbed in cyclohexane following neutralization, the sodium salt of the behinic acid was filtered off and washed with cyclohexane. Recovery of the solutions by distillation yielded 390 gm of ester, i.e., the yield was 75 percent of theoretical.

EXAMPLE A (Comparative Example)

(Lauryl chloride conversion with sodium acetate)

205 gm (2.5 moles) of sodium acetate; 15 gm (10 mole percent with respect to salt) of acetic acid; and 614 gm (3.0 moles) of lauryl chloride are heated for 4 hours to 230°C, 11 gm of low boiling point product being distilled off as a whole. Recovery is undertaken in conventional manner. Separating the lauryl chloride ($K_{p13}$ 136°–143°C) from the lauryl acetate ($K_{p10}$ 148°C) by distillation is not feasible because the boiling points are too close together. Therefore the chlorine content is determined from the oil phase. Said content is 16.7 percent, i.e., only very slightly below that of pure lauryl chloride (17.4 percent).

The experiment is repeated by using 10 mole percent 2-ethylhexanoic acid in lieu of acetic acid and in taking water out of circulation (1.5 mole) during the reaction. In this manner the mixture remains fluid and stirrable. Following conventional recovery, the chlorine content amounts to 13.7 percent, i.e., in this example too, conversion is too low.

EXAMPLE B (Comparative Test)

244 gm (3.3 mole) of propionic acid; 240 gm (3.0 moles) of sodium hydroxide (50 percent); and 150 gm of water are stirred and this solution is added while stirring to 716 gm (3.5 moles) of lauryl chloride heated to 200°C, in such manner that the excess water can be taken out of circulation. The acid that is carried along is replaced by 20 gm of fresh propionic acid. The mixture so obtained is heated while stirring for 2 more hours at 210°C, and following distilling off low boiling components, 2 more hours at 235°C while stirring. Following washing with water, distillation is undertaken.

Only 88 gm of ester has been generated, i.e., yield is only 11 percent of theoretical.

EXAMPLE 6

A paraffin cut, 97 percent straight-chain, consisted of the following:

| | | |
|---|---|---|
| n-C 11-alkane | 0.2 | percent |
| n-C 12-alkane | 71.9 | percent |
| n-C 13-alkane | 24.1 | |
| n-C 14-alkane | 0.5 | |
| | 96.7 | percent | and is chlorinated conventionally to a chlorine content of 6.76 percent. Then the product is distilled in a one meter heated glass column (filled with glass Raschig rings) under various conditions; the temperatures during the first distillation are so low that no decomposition of the chloroalkanes occurs (see Table 1 following) because according to the analytical values, olefins have occurred only in very minute amounts; the second fraction consists of 65 percent monochloroalkanes and according to gas chromatographic analysis, these contain 10.7 percent of 1-chloroalkanes referred to the sum of the chloroalkanes (see Table 2 following).

According to the bromine numbers, dissociation of the chloroalkanes occurs during the second distillation because of the higher temperatures (see Table 1). Fractions 4, 5 and 6 of this distillation contain the total monochloroalkanes and are introduced together. The proportion of 1-chloroalkanes referred to the sum of the chloroalkanes according to the gas chromatographic analysis amount to 17.4 percent (see Table 2); thus almost twice as large as for the first distillation.

This kind of distillation goes on continuously and the 1-chloroalkanes further grows in the sump of the distillation or decomposition column; after appreciable time, sump products are obtained with compositions per gas chromatographic analysis that are listed in Table 3 following; the reactor temperatures at this latter time are set for 300°–350°C.

TABLE 1

Fractionating the Chlorination Product

| | Head Temp. | Sump Temp. | Torr (mmHg) | Weight | Chlorine content | Bromine Content | Fraction composition per gas chromatographic analysis (Cf Table 2) |
|---|---|---|---|---|---|---|---|
| Fr. 1 | 91–194 | 117–134 | 9 | 1029 g = 52.3% | 420 ppm | 0.23 | Paraffins |
| Fr. 2 | 104–142 | 134–185 | 9–7 | 814 g = 41.3% | 11.45% | 0.92 | 65% Monochloralkanes and Paraffins |
| Residue | | | | 101 g = 5.1% | 30.85 | | — |
| Fr. 1 | 142–146 | 155–170 | 100 | 880 g = 44.0% | 0.2% | 25.3 | Paraffins and Olefins |
| Fr. 2 | 146–153 | 171–176 | 100 | 206 g = 10.3% | 0.26% | 13.2 | |
| Fr. 3 | 155–162 | 176–182 | 100 | 329 g = 16.5% | 0.73% | 18.7 | |
| Fr. 4 | 162–173 | 184–190 | 100 | 208 g = 10.4% | 6.50% | 22.6 | 59% Monochloralkanes and Paraffins & Olefins |
| Fr. 5 | 174–185 | 190–205 | 100 | 276 g = 13.8% | 14.4% | 25.5 | |
| Fr. 6 | 172–175 | 211–236 | 40 | 50 g = 2.5% | 21.7% | 21.6 | |
| Residue | | | | 31 g = 1.5% | 28.8% | | — |

TABLE 2

Gas chromatographic analysis of the chloroalkane fractions

| | 1st distillation fraction No. 2 (41% of the ester) | 2nd distillation fraction Nos. 4, 5 and 6 (additional 7% of the ester) |
|---|---|---|
| C-12 – 14 Paraffins | 33.5% + Zwlf.[+) | 35.6% + Zwlf.[+) |
| 6-C – 12 Chloroalkane | 10.3%) | 7.5%) |
| 5-C – 12 Chloroalkane | 6.8%) | 5.0%) |
| 4-C – 12 Chloroalkane | 8.6%) | 7.9%) |
| 3-C – 12-Chloroalkane | 9.8%) | 8.7%) |
| 2-C – 12-Chloroalkane | 9.1%) | 12.8%) |
| 1-C – 12 Chloroalkane | 5.4%) | 8.5%) |
| | 65.2% | 59.3% |
| 7-C + 6-C-13-Chloroalkane | 3.6%) | 1.3%) |
| 5-C – 13-Chloroalkane | 2.4%) | 1.0%) |
| 4-C – 13-Chloroalkane | 2.4%) | 1.3%) |
| 3-C – 13-Chloroalkane | 2.5%) | 1.2%) |
| 2-C – 13-Chloroalkane | 2.7%) | 2.3%) |
| 1-C – 13-Chloroalkane | 1.6%) | 1.8%) |
| High boiling point substances | 1.2%) | 1.3%) |
| | 99.9% | 96.2% |
| 1-chloroalkane portion with respect to the sum of the chloroalkanes | 10.7% | 17.4% |

[+)Zwlf. = intermediate runs that cannot be assigned.

TABLE 3

Decomposition reactor sump product analysis

| Sump product | A | B | C |
|---|---|---|---|
| Acid number | 0.02 | 0.01 | 0.05 |
| Bromine number | 23.8 | 22.0 | 13.4 |
| Chlorine content | 4.76% | 9.34% | 11.2% |
| Chlorine content in 1-chloroalkanes from IR spectrum and computed as lauryl chloride | about 19% | 43% | 55% |
| GAS CHROMATOGRAPHIC ANALYSIS | | | |
| Carbons | 68.5% | 38.1% | 34.8% |
| Intermediate run 1 | 8.1 | 5.7 | 5.0 |
| n-C12 chloroalkane | 10.3 | 27.1 | 38.6 |
| Intermediate run 2 | 5.0 | 8.2 | 4.3 |
| n-C13 chloroalkane | 6.2 | 16.0 | 14.6 |
| Intermediate run 3 | 1.5 | 4.2 | 1.7 |
| n-C14 chloroalkane | 0.2 | 0.4 | 0.5 |
| High boiling point substances | 0.2 | 0.4 | 0.4 |

As shown by Table 3, chlorine contents and concentrations in 1-chloroalkanes increase together, that is, there is enrichment in the desired compounds. It could not be ascertained which were the substances in the intermediate stages or runs.

The following experiments were carried out with that product which had a chlorine content of 11.2 percent as a consequence of enrichments. This substance is denoted as sump product C below.

EXAMPLE 7

1,585 gm of sump product (chlorine content = 11.2 percent) and 680 gm of sodium salt of 2-ethylhexanoic acid (97.2 percent, the remainder of 2.8 percent being a free acid) are heated in a nitrogen atmosphere for 2 hours at 220°C and with stirring. Following cooling, the precipitated sodium chloride, which also might be easily filtered out, is dissolved in one liter of water and the aqueous salt solution is removed. According to the acidity figure, no acid is present in said solution and again, no salt could be shown from the 2-ethylhexanoic acid. Thus both components remain in the organic phase and are not lost with the drainage.

The crude ester is then neutralized according to an acid number of 7.44 with 228 gm of 10 percent sodium hydroxide and thereupon is distilled. Products in an amount of 738 gm are obtained as the first fraction $K_p$ $_{0.4}$ 48°–140°C (mainly paraffins, olefins and chlorine compounds), which failed to react. The second fraction of 1,142 gm consists of esters of the 2-ethylhexanoic acid $K_p$ $_{0.4}$ 140°–150°C, 51 gm remaining as residue. The ester yield (molecular weight = 315) is therefore 91 percent of theoretical with respect to the sodium salt used.

Saponification takes place conventionally and is carried out in three different manners (see Examples 8, 9 and 10) for recovery of the 2-ethylhexanoic acid.

EXAMPLE 8

638 gm (2.0 moles) of ester together with 88 gm (2.2 moles) of sodium hydroxide and 40 gm of water are heated for 4 hours at reflux, the temperature being raised from 125° to 135°C. The mixture does not foam and allows good stirring. Following cooling, it is diluted with water; recovery taking place in conventional manner by means of cyclohexane as the extracting means. Distillation provides 377 gm of alcohol, or 99 percent of theoretical. The alcohol held 520 ppm of chlorine, a bromine number of 11.5 and, according to gas chromatographic analysis is made up as follows:

| | |
|---|---|
| undecanol-1 | 0.7% |
| dodecanol-1 | 71.3% |
| tridecanol-1 | 16.6% |
| unsaturated alcohols of unknown structures | 11.4% |
| | 100.0% |

Upon hydrogenation, the substance's composition is as follows:

| | |
|---|---|
| undecanol-1 | 0.9% |
| dodecanol-1 | 78.4% |
| tridecanol-1 | 18.9% |
| unknown alcohols | 1.9% |
| | 100.0 |

Therefore the content of straight-chain alcohols exceeds 98 percent.

EXAMPLE 9

630 gm of ester are heated with 40 gm of sodium hydroxide and 20 gm of water for 4 hours at reflux at about 130°C. The reaction mixture is directly distilled, the water being separated as a first run. The yield, 99 percent of theoretical, is 187 gm of alcohol. The composition corresponds to the above analytical data.

The distillation residue contains the sodium salt of the 2-ethylhexanoic acid dissolved in the non-reacted ester or suspended in colloidal form. Losses in this salt are minute because the mixture recovery following dilution with water and cyclohexane as extracting means results in an aqueous solution from which 140 gm of 2-ethylhexanoic acid or 97 percent of theoretical are recovered by acidification with sulfuric acid.

EXAMPLE 10

An aqueous solution consisting of 240 gm (3.0 moles) of 50 percent sodium hydroxide and 475 gm (3.3 moles) of 2-ethylhexanoic acid is added to 1,100 gm (3.5 moles computed from the chlorine content) of sump product C, whereupon stirring and heating to 200°C follows. Upon adding the salt solution, the water is distilled off and is eliminated by means of a water decirculator. The mixture is then heated to 220°C with stirring for two hours. Following cooling, the precipitated cooking salt is washed off with 700 ml of water and the excess acid is neutralized with 82 gm of 25 percent sodium hydroxide solution, and the salt solution is removed.

1,353 gm of reaction products are distilled. There is a first run of non-converted chlorine compounds, paraffins and olefins in an amount of 467 gm (boiling point range of 8 torr (mm Hg) is 80° – 191°C). 874 gm of crude ester are obtained, which is saponified without further purification.

457 gm of a high boiling point distillation residue are added to 864 gm (2.75 moles) of crude ester, said residue consisting of the oxosynthesis of C13/14 (linear) olefins and which according to the hydroxyl number (about 110) and the saponification number (about 5–10) is made up of long-chain alcohols. The mixture is heated together with 252 gm of 50 percent sodium hydroxide solution (= 3.15 moles) for 3 hours while stirring, up to boiling, at reflux (temperature about 120°C).

Thereupon the water is first distilled off, then the alcohol at 9 torr (mm Hg) and 133°–150°C. Yield is 485 gm or 93.4 percent of theoretical (molecular weight of the alcohol = 189).

EXAMPLE 11

As regards Example 10, a solution of the sodium salt of the 2-ethylhexanoic acid had been obtained in the high boiling point distillation residue of a C13-14 oxoalcohol. This solution is reacted with sump product C, by stirring 926 gm of the salt solution, which contains 484 gm of sodium salt, with 1,070 gm (3.42 moles computed from the chlorine content) of sump product C and heating to 220°C. Thereupon sufficient 2-ethylhexanoic acid is added to obtain an acid number of 6.0. Cooling is applied after 2 hours, the cooking salt is washed with water and the free acid with sodium hydroxide solution out of the crude product, the latter again being distilled in such manner that the non-esterified proportions are removed (amount = 485 gm; boiling point range at 10 torr (mm Hg) from 38 to 195°C). 1,270 gm of distillation residue had been generated in this distillation, of which 442 are of high boiling point and 828 gm are ester; therefore the yield is 90 percent of theoretical with respect to the sodium salt.

Saponification is carried out in known manner with 50 percent sodium hydroxide solution and the recovery is performed by distillation (see Example 10). The composition of the alcohol is similar to that of the described examples.

The generated sodium salt of the 2-ethylhexanoic acid is again reacted with the decomposition product C etc.

EXAMPLE 12

330 gm of the sodium salt (3.0 moles) of isobutyric acid are mixed with 1,102 gm (3.5 moles) of sump product C and sufficient isobutyric acid is added until an acid number of 4.5 is obtained. This mixture is heated for 3 hours to 230°C with stirring. Following cooling the cooking salt is washed with water and the acid with 25 percent sodium hydroxide solution. Distillation provides 659 gm of ester (molecular weight = 258) in a boiling point range from 154 to 168°C at 15 torr (mm Hg); the yield therefore is 85.3 percent of theoretical. Saponification takes place in exothermal manner and quantitatively, the 50 percent sodium hydroxide solution being applied dropwise to the ester raised to 130°C at such a rate that the temperature does not excessively increase. Following one hour of stirring, the reaction product is recovered by distillation and yields the alcohol in the described composition.

EXAMPLE 13

A 98 percent straight-chain paraffin cut consists of the following:

| | |
|---|---|
| n-C 10-alkane | 4.0% |
| n-C 11-alkane | 93.9% |
| n-C-12-alkane | 1.5% |
| | 99.4% | and is chlorinated in conventional manner to a chlorine content of 6.87 percent. Thereupon the product is distilled and, as explained in greater detail in Example 6, continuously transmitted into the olefin-paraffin mixture in the decomposition reactor. A product is accumulated in the sump of the dissociation reactor and a sample is taken from said product following a fairly short and a fairly long time of operation (see Example 15); said sample is called sump product D.

Said sample is reacted as follows:

1,831 gm (3.3 moles computed from the 6.4 percent chlorine content) of sump product D are mixed with 498 gm (3.0 moles) of the sodium salt of 2-ethylhexanoic acid and with 22 gm of 2-ethylhexanoic acid and heated at reflux for 3 hours with a stirring to 206°C. Following cooling the cooking salt is removed from the reaction product with water and the excess acid with sodium hydroxide solution.

Distillation yields 413 gm of ester in a boiling point range of 165° – 193°C at 11 torr (mm Hg), i.e., the yield is 46.1 percent with reference to the sodium salt used. 300 gm of a product mixture with a boiling point range of 90° – 180°C at 11 torr (mm Hg) contains 13 percent of chlorine and has not been converted.

Ester saponification takes place in the manner described with respect to the 2-ethylhexanoic acid esters: 189 gm of alcohol are obtained by distillation from 345 gm (1.16 moles; alcohol molecular weight = 172) of ester. The boiling point range is 124° – 126°C at 7 torr (mm Hg), the yield is 95 percent of theoretical.

The chlorine content of the alcohol is 0.23 percent and according to gas chromatographic analysis the alcohol consists of:

| | |
|---|---|
| first run | 0.3% |
| decanol-1 | 1.0% |
| undecanol-1 | 79.0% |
| dodecanol-1 | 0.8% |
| unsaturated n-alcohols (with analogous C-numbers) | 18.8% |
| | 99.9% |

Thus the alcohol is 99 percent straight-chain.

The relatively low yield is explained by the proportion of 1-chloroalkanes still being minor even though fairly large amounts of chlorine compounds are present in the sump of the dissociation reactor after fairly short operation times.

EXAMPLE 14

A product accumulating in the sump of the decomposition reactor over fairly long operational times in the embodiment described in Example 13 is removed from the sump. The chlorine content of this so-called sump product is 14.1 percent (and shows an enrichment in chlorine compounds as the operation times of the decomposition reactor increase).

461 gm (3.2 moles) of 2-ethylhexanoic acid and 248 gm (3.1 moles) of 50 percent sodium hydroxide solution are mixed and added dropwise to 908 gm (3.6 moles as computed from the 14.1 percent chlorine content) of sump product E that has been heated with stirring to 200°C. The water is distilled off in this procedure. After one hour, the addition of the salt solution is terminated and the reaction mixture is heated further to 220°C for 2 hours with stirring. Following cooling, the cooking salt is washed off with water and the acid with 25 percent sodium hydroxide solution. Distillation yields 860 gm of ester; the yield therefore is 90 percent of theoretical.

EXAMPLE 15

The sodium salt of an acid mixture is used in this experiment, which consists of 80 percent of a straight-chain 8 carbon carboxylic acid and of 20 percent of a straight-chain 10 carbon carboxylic acid (this is an industrial product which is commercially available). The 91 percent sodium salt of the acid mixture so obtained has an acid number of 33.0.

133 gm (0.7 mole) of the sodium salt and 263 gm (0.84 mole as computed from the 11.3 percent chlorine content) of a sump product prepared as described in Example 13 but removed from the reactor facility after an appreciable time of operation, are heated with stirring for 4 hours to 210°C. The cooking salt and the acid again are to be respectively washed off after cooling with water and sodium hydroxide solution, but separation problems occur in both respects because part of the organic phase has been emulsified in the aqueous washing solution (obviously on account of the surface activity of the sodium salts). Therefore the washing solutions have to be extracted. Cyclohexane is used to that end, being distilled off following extraction. The distillation residue is combined with the main amount of reaction product and distilled. An ester fraction of 156 gm (molecular weight = 306) is obtained for a boiling point range from 190° to 199°C at 9 torr (mm Hg); the yield therefore is 73.7 percent of theoretical.

We claim:

1. In a process for preparing straight-chain, primary alcohols having 6 – 20 carbon atoms, the improvement comprising: reacting at a temperature of about 150° to 300°C straight-chain 1-chloroalkanes having 6 to 20 carbon atoms with alkali salts of alkanoic acids having 4 to 22 carbon atoms in the presence of 1 to 10 mole percent of alkanoic acids based on said alkali salts of the alkanoic acids to form esters, saponifying said esters in an alkaline medium to form straight-chain, primary alcohols having 6 – 20 carbon atoms and separating said straight-chain, primary alcohols.

2. In a process for preparing straight-chain, primary alcohols having 6 – 20 carbon atoms, comprising:
  a. chlorinating straight-chain paraffins having 6 to 20 carbon atoms to form chlorinated paraffins;
  b. dehydrochlorinating and fractionally distilling said chlorinated paraffins; the improvement comprising:
  c. separating straight-chain 1-chloroalkanes having 6 to 20 carbon atoms as a sump product;
  d. reacting said straight-chain 1-chloroalkanes with alkali salts of alkanoic acids having 4 to 22 carbon atoms in the presence of 1 to 10 mole percent of alkanoic acids having 4 to 22 carbon atoms and at a temperature of about 150° to 300°C to form esters;
  e. saponifying said esters in an alkaline medium to form said straight-chain, primary alcohols having 6–20 carbon atoms; and
  f. separating said straight-chain, primary alcohols.

3. The process of claim 2, wherein said alkali salts of alkanoic acids have 4 to 10 carbon atoms.

4. The process of claim 3, wherein said reacting temperature is about 200° to 250°C.

5. The process of claim 2, wherein step (d) is carried out for a period of about 10 minutes to 5 hours.

6. The process of claim 5, wherein step (d) is carried out for a period of about 1 to 2 hours.

7. The process of claim 2, wherein said 1-chloroalkanes have a chlorine content of about 11 to 29 percent and are selected from the group consisting of lauryl chloride, 1-chloro-undecane, n-hexyl-chloride, 1-chloro-C20 alkane, 1-chloro-C22 alkane, mixtures of C-11 to C-14 1-chloroalkanes, 1-chloro-octane, 1-chloro-nonane, 1-chloro-decane, 1-chloro-tridecane, 1-chloropentedecane, 1-chloro-hexadecane, 1-chloro-heptadecane, 1-chloro-nonadecane and mixtures thereof.

8. In a process for preparing straight-chain, primary alcohols comprising dehydrochlorinating a solution consisting essentially of higher paraffinic hydrocarbons and not more than about 50 percent based on the total moles in solution of monochlorinated higher paraffinic hydrocarbon, said dehydrochlorinating comprising subjecting said solution to reflux fractional distillation at 100° – 500°C in the presence of a metallic iron catalyst; the improvement comprising:
  a. separating straight-chain 1-chloroalkanes having 6 to 20 carbon atoms as a sump product in said reflux fractional distillation;
  b. reacting said straight-chain 1-chloroalkanes with alkali salts of alkanoic acids having 4 to 22 carbon atoms in the presence of 1 to 10 mole percent of alkanoic acids corresponding to the alkanoic structure of said alkali salts and at a temperature of about 150° to 300°C to form esters;
  c. saponifying said esters in an alkaline medium to form straight-chain, primary alcohols having 6–20 carbon atoms; and
  d. separating said straight-chain, primary alcohols.

* * * * *